United States Patent
Chen

(10) Patent No.: US 11,593,158 B2
(45) Date of Patent: Feb. 28, 2023

(54) UNIVERSAL PERIPHERAL EXTENDER FOR COMMUNICATIVELY CONNECTING PERIPHERAL I/O DEVICES AND SMART HOST DEVICES

(71) Applicant: Kingston Digital Inc., Fountain Valley, CA (US)

(72) Inventor: Ben Wei Chen, Fountain Valley, CA (US)

(73) Assignee: KINGSTON DIGITAL INC., Fountain Valley, CA (US)

( * ) Notice: Subject to any disclaimer, the term of this patent is extended or adjusted under 35 U.S.C. 154(b) by 243 days.

(21) Appl. No.: 16/896,917

(22) Filed: Jun. 9, 2020

(65) Prior Publication Data

US 2021/0382749 A1 Dec. 9, 2021

(51) Int. Cl.
| | |
|---|---|
| G06F 9/48 | (2006.01) |
| G06F 1/24 | (2006.01) |
| G06F 9/30 | (2018.01) |
| G06F 11/07 | (2006.01) |
| G06F 13/12 | (2006.01) |
| G06K 7/04 | (2006.01) |

(52) U.S. Cl.
CPC .............. *G06F 9/4881* (2013.01); *G06F 1/24* (2013.01); *G06F 9/30065* (2013.01); *G06F 11/0772* (2013.01); *G06F 13/126* (2013.01); *G06K 7/042* (2013.01)

(58) Field of Classification Search
CPC ...... G06F 1/1632; G06F 1/1633; G06F 3/038; G06F 3/023; G06F 1/24; G06F 9/4881; G06F 9/4887; G06F 9/4893; G06F 9/50
See application file for complete search history.

(56) References Cited

U.S. PATENT DOCUMENTS

| | | | |
|---|---|---|---|
| 6,208,904 B1 | 3/2001 | Mullen, Jr. | |
| 6,222,855 B1 | 4/2001 | Kimber et al. | |
| 8,190,798 B1* | 5/2012 | Dalal | G06F 13/14 |
| | | | 710/72 |
| 9,213,661 B2* | 12/2015 | Coneski | G06F 13/385 |
| 2006/0238791 A1* | 10/2006 | Jiang | 358/1.13 |

(Continued)

FOREIGN PATENT DOCUMENTS

| | | |
|---|---|---|
| AU | 2016100189 B4 | 8/2017 |
| TW | 200622620 A | 7/2006 |

(Continued)

OTHER PUBLICATIONS

TW Office Action dated Jan. 26, 2022, Appl. No. 109146274, 24 pages.

(Continued)

*Primary Examiner* — Raymond N Phan
(74) *Attorney, Agent, or Firm* — Brundidge & Stanger, P.C.

(57) ABSTRACT

A universal peripheral extender architecture, system, and method is disclosed that addresses the need of communicatively connecting peripheral I/O devices and the smart host devices in legacy, medical, and industrial applications. As disclosed, a universal peripheral extender includes an I/O device translation & management module that has a device-side utility, a host-side I/O device translation & management utility, and a host/device translation & management scheduler utility.

11 Claims, 10 Drawing Sheets

(56) References Cited

U.S. PATENT DOCUMENTS

| | | | |
|---|---|---|---|
| 2007/0038785 A1 | 2/2007 | Varanda et al. | |
| 2008/0248672 A1 | 10/2008 | Yip | |
| 2011/0219163 A1 | 9/2011 | Beadnell et al. | |
| 2011/0264835 A1 | 10/2011 | Chen et al. | |
| 2012/0011287 A1* | 1/2012 | Zeung | G06F 1/1632 |
| | | | 710/16 |
| 2014/0013014 A1 | 1/2014 | Huang et al. | |
| 2014/0059264 A1* | 2/2014 | Sudak | G06F 1/1632 |
| | | | 710/303 |
| 2015/0271658 A1* | 9/2015 | Huang | H04L 67/12 |
| | | | 455/39 |
| 2016/0224065 A1 | 8/2016 | Weldon | |
| 2018/0329837 A1 | 11/2018 | Mishra et al. | |
| 2018/0353869 A1* | 12/2018 | Corkin | A63H 5/00 |
| 2019/0080730 A1 | 3/2019 | Lee | |

FOREIGN PATENT DOCUMENTS

| | | |
|---|---|---|
| TW | 201234197 A | 8/2012 |
| TW | M592993 U | 4/2020 |

OTHER PUBLICATIONS

Combined Search and Examination Report from GB Application No. 2011699.2 dated Jan. 13, 2021, 3 pages.

\* cited by examiner

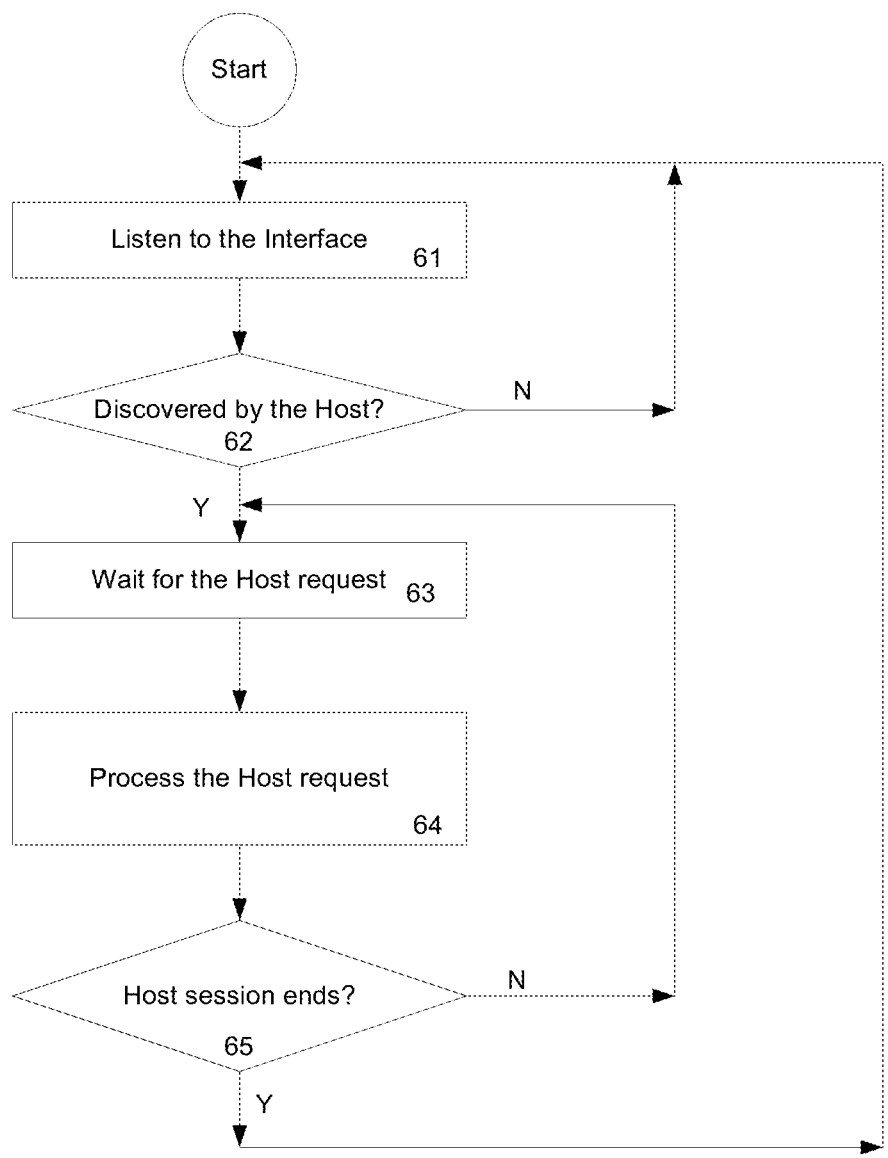
FIG. 6 Device Control Utility

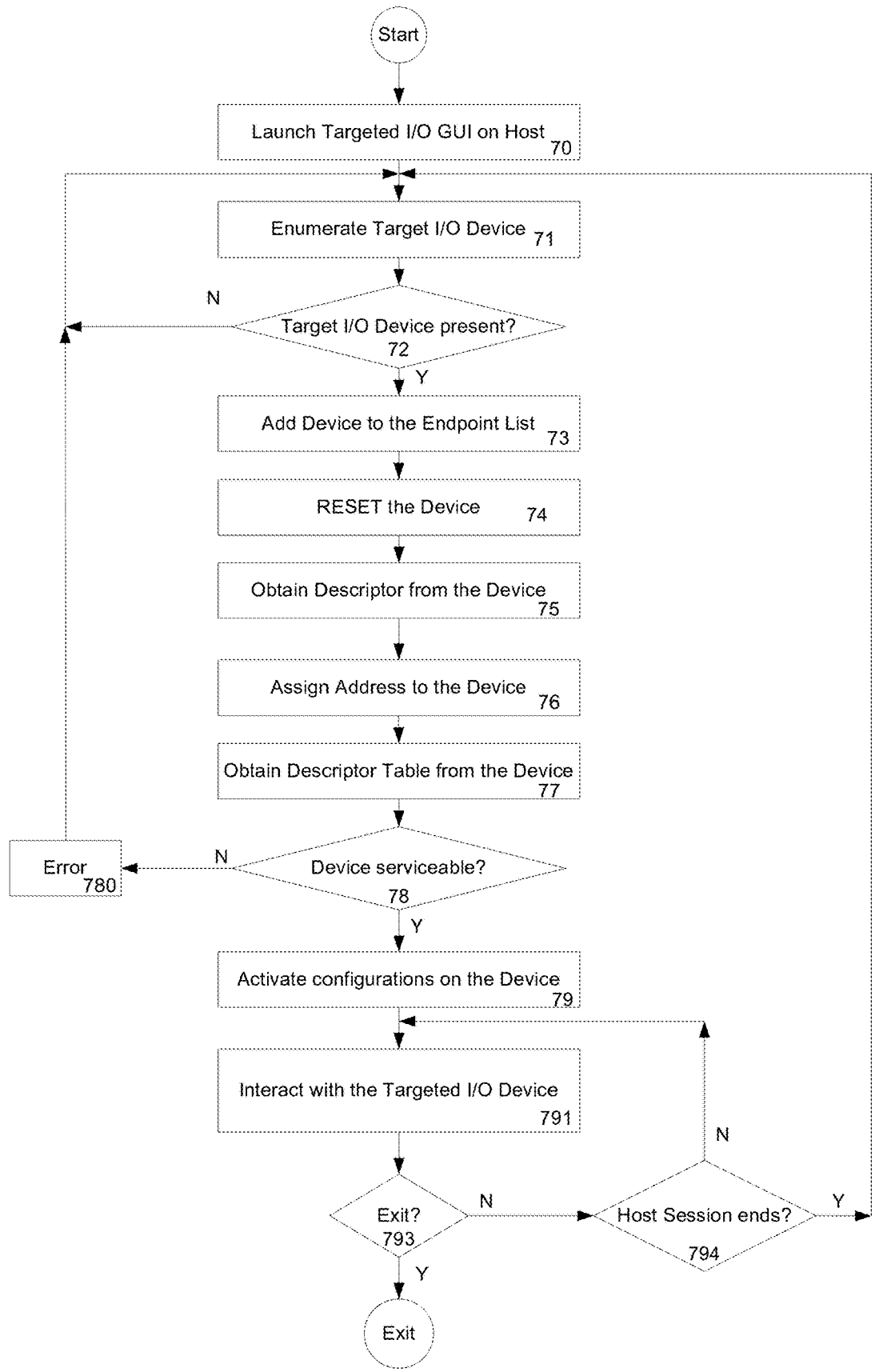
FIG. 7 Smart Host Application Utility

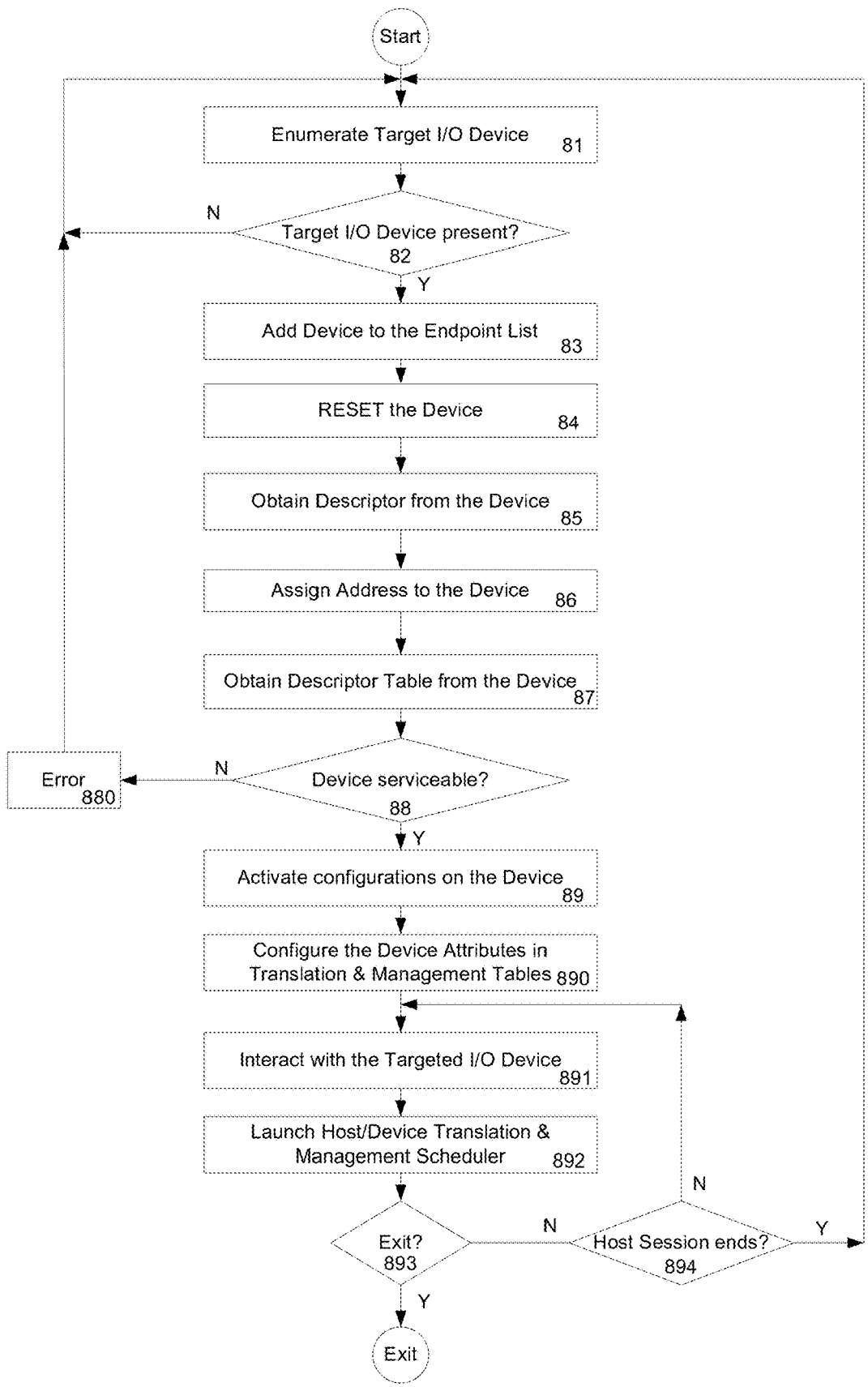
FIG. 8 Device-side I/O Device Translation & Management Utility

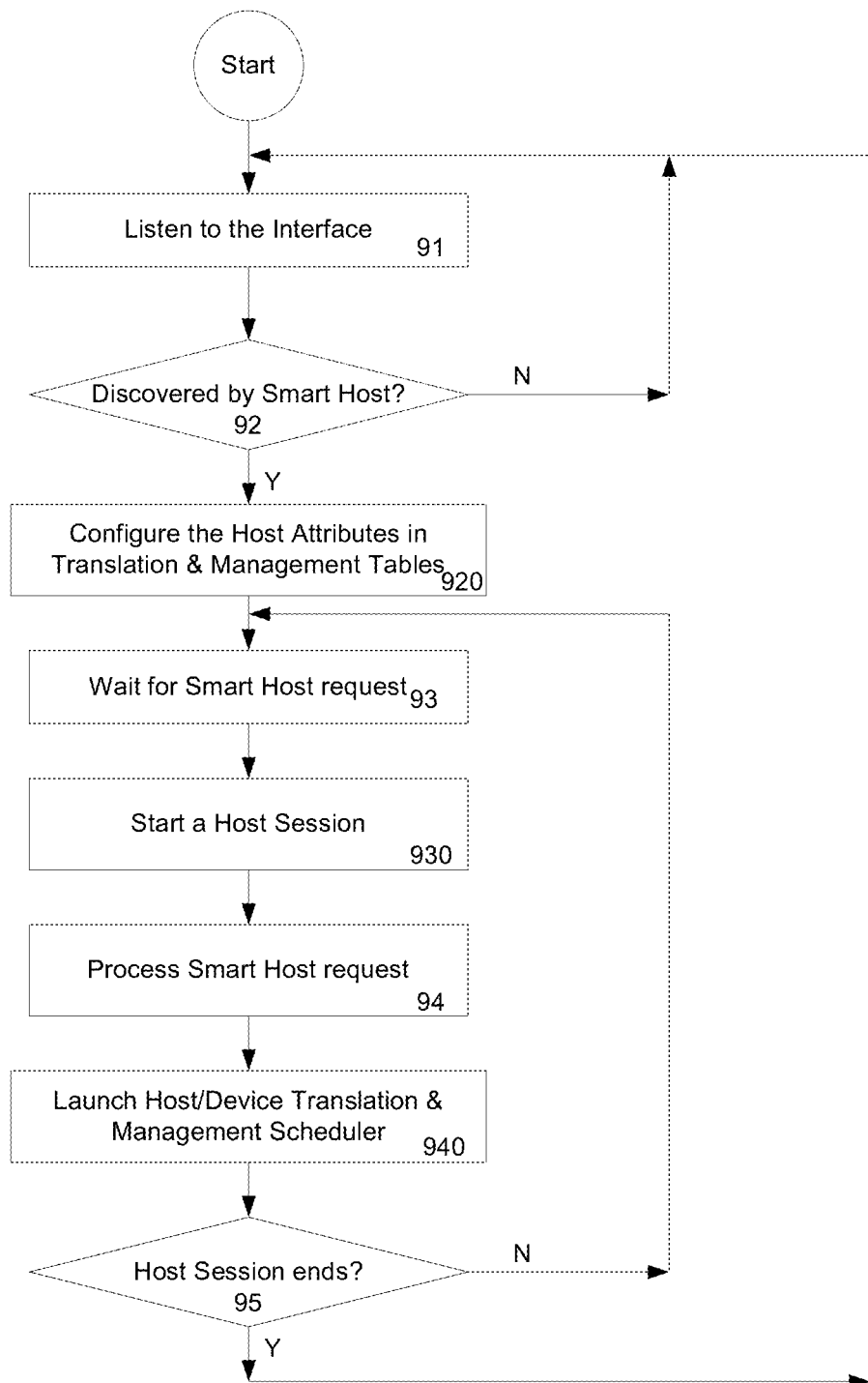
FIG. 9 Host-side I/O Device Translation & Management Utility

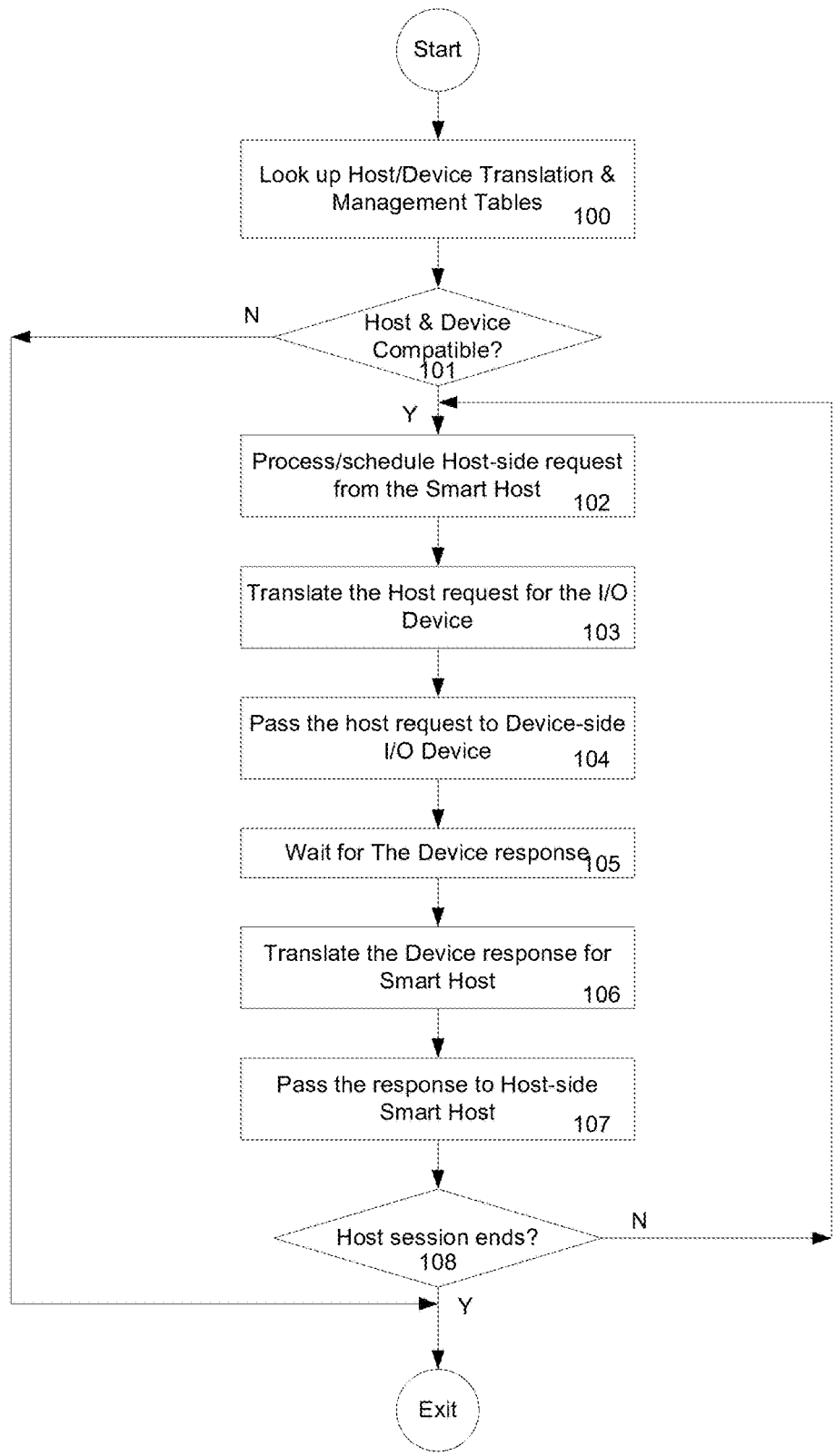
FIG. 10 Host/Device Translation & Management Scheduler Utility

UNIVERSAL PERIPHERAL EXTENDER FOR COMMUNICATIVELY CONNECTING PERIPHERAL I/O DEVICES AND SMART HOST DEVICES

FIELD OF THE INVENTION

The present invention relates generally to a universal peripheral extender architecture, system, and method.

BACKGROUND OF THE INVENTION

There are many interfaces and peripheral Input/Output (I/O) devices introduced since the PC first became available more than forty years ago. These interfaces, including USB-A, PCIe, SATA, Ethernet, WiFi, Bluetooth, USB-C, Lightning, Thunderbolt, HDMI, and others, survived and grew during the PC evolution. The corresponding legacy peripheral I/O devices include USB storage, SSD, keyboard, mouse, track pad, display panel, headset, speaker, sports bracelet, IP camera, printer, scanner, media card reader, Blu-ray/DVD burner, smart card reader and other smart peripherals. The peripheral I/O devices in medical or industrial applications include endoscope, ultrasonic instrument, X-Ray, Electrocardiography (ECG) instrument, non-invasive blood glucose meter, Point-of-sale system, Contactless infrared thermometer, sphygmomanometer, AI co-processor, and others.

When a smart host such as a smart phone and tablet became more ubiquitous than the PC or notebook in average people's daily life, there is a great need for a layman to be able to access the existing peripheral I/O devices from the smart phone in the pocket or the tablet at hand, instead of having to wait until reaching a bulky notebook at home or in office.

An example of a general-purpose smart host is composed of: sufficient computing power, real-time OS and device drivers, battery system to make it portable, display panel for user interface I/O, a plurality of interface channels for network and media connections and the ability to connect to the web/AI for data collection, analysis and optimization One example usage is for a user to access the Europay, Mastercard, Visa (EMV) chip card through a smart card reader. Currently, there is no problem in accessing the USB-based smart card reader on the notebook or PC platforms, as the USB interface is available as well as the required device driver and the corresponding application utility. But when it comes to the smart host platform, neither the interface, nor the application utility, let alone the device driver is available. Therefore, the average user has to rely heavily on the legacy notebook or PC, whenever access to the traditional peripheral I/O device is required, such as the case with the smart card reader cited above, even if the smart host is more readily at hand. This type of frustration can be exemplified by the fact that even the standard type of USB storage had just started being supported on the iOS platform, ten years after the iPhone/iPad was introduced. Similarly, while an off-the-shelf Bluetooth mouse is full-functioned and easy to use in today's Windows Office environment, its right-click, scroll-wheel and mouse-pointer functions are still yet to be supported in the Remote Desktop application on today's iOS environment.

Compared with the fast-evolving nature of the smart hosts, the medical and industrial platforms, are even relatively more conservative in adopting new technology standards, particularly in the interface areas. The peripheral I/O devices in medical and industrial applications are therefore less likely to be natively supported on the smart host platforms. But with the ubiquity, omnipresent nature of the smart host, combined with its high performance in computing power and affordable price, it is very beneficial to employ and deploy the smart host as the intuitive user interface between the user and many peripheral I/O devices, including the legacy, medical, and industrial peripheral I/O devices.

Accordingly, what is needed is a universal peripheral extender architecture and system that addresses the above identified issues of connecting the general-purpose peripheral I/O devices and the general-purpose smart host in legacy, medical, and industrial applications. The present application addresses such a need.

SUMMARY OF THE INVENTION

A universal peripheral extender architecture and system is disclosed which addresses the need in connecting the general-purpose peripheral I/O devices and the general-purpose smart host in legacy, medical, and industrial applications.

In one example, the universal peripheral extender system includes a universal peripheral extender; at least one interface channel; at least one smart host; at least one peripheral I/O device; at least one power source; and at least one corresponding application utility associated with at least one target I/O device, respectively; wherein the universal peripheral extender is communicatively coupled, via the at least one interface channel to: the at least one smart host, the target I/O device, and the at least one power source, respectively; wherein the at least one peripheral I/O device includes the at least one peripheral I/O device, respectively; and wherein the corresponding application utility associated with the target I/O device is installed in the at least one smart host to perform a function of the target I/O device.

In another example, a universal peripheral extender, including an I/O device translation & management module has a device-side utility; a host-side I/O device translation & management utility; and a host/device translation & management scheduler utility.

In another example, a non-transitory computer-readable medium storing executable instructions to communicatively connect a target I/O device and smart host by an I/O device translation & management module of a universal peripheral extender so that, in response to execution, cause a computing device of the universal peripheral extender to execute a device-side utility of the I/O device translation & management module to perform operations including: enumerating the target I/O device; conducting a check to determine if the target I/O device is present; in response to the target I/O device not being present, returning the operations to the enumerating the target I/O device; in response to the target I/O device being present, adding the target I/O device to the endpoint list; issuing a RESET command to the target I/O device; obtaining a Descriptor from the target I/O device; assigning a device address to the target I/O device; obtaining a Descriptor table from the target I/O device; conducting a check to determine if the target I/O device is serviceable; in response to the target I/O device not being serviceable, then encountering an error and the process returns to the enumerating the target I/O device; in response to the target I/O device not being serviceable, then activating configurations on the target I/O device; configuring target I/O device attributes in target I/O device translation & management tables; interacting with the targeted I/O device; launching a host/device translation & management scheduler; conducting a check to determine if the application utility is to end;

in response to the application utility ending, the application utility exits; in response to the application utility continuing, conducting another check to determine if the host session ends; in response to the host session ending, returning the operation to enumerating the target I/O device; and in response to the host session continuing, continue interacting with the target I/O device.

Additional aspects, advantages and features of the present invention are included in the following description of exemplary examples thereof, which description should be taken in conjunction with the accompanying drawings.

BRIEF DESCRIPTION OF THE DRAWINGS

The accompanying figures illustrate several examples of the invention and, together with the description, serve to explain the principles of the invention. One of ordinary skill in the art readily recognizes that the examples illustrated in the figures are merely exemplary, and are not intended to limit the scope of the present invention.

FIG. 6 illustrates an example of the device control utility.

FIG. 7 illustrates an example of the smart host application utility.

FIG. 8 illustrates an example of the device-side I/O device translation & management utility.

FIG. 9 illustrates an example of the host-side I/O device translation & management utility.

FIG. 10 illustrates an example of the host/device translation & management scheduler utility.

DETAILED DESCRIPTION

The present invention relates generally to portable data accessing devices and more particularly to the use of multi-port interfaces on a data accessing device. Detailed examples or embodiments of the claimed structures, methods, and system are disclosed herein; however, it can be understood that the disclosed examples or embodiments are merely illustrative of the claimed structures and methods that may be embodied in various forms. This invention may, however, be embodied in many different forms and should not be construed as limited to the examples or embodiments set forth herein. In the description, details of well-known features and techniques to those skilled in the art may be omitted to avoid unnecessarily obscuring the presented examples or embodiments.

References in the specification to "one embodiment", "an embodiment", "an exemplary embodiment", "one example," "an example," etc., indicate that the example or embodiment described may include a particular feature, structure, or characteristic, but every example or embodiment may not necessarily include the particular feature, structure, or characteristic. Moreover, such phrases are not necessarily referring to the same example or embodiment. Further, when a particular feature, structure, or characteristic is described in connection with an example or embodiment, it is submitted that it is within the knowledge of one skilled in the art to affect such feature, structure, or characteristic in connection with or in combination with other examples or embodiments whether or not explicitly described.

Figure 1:
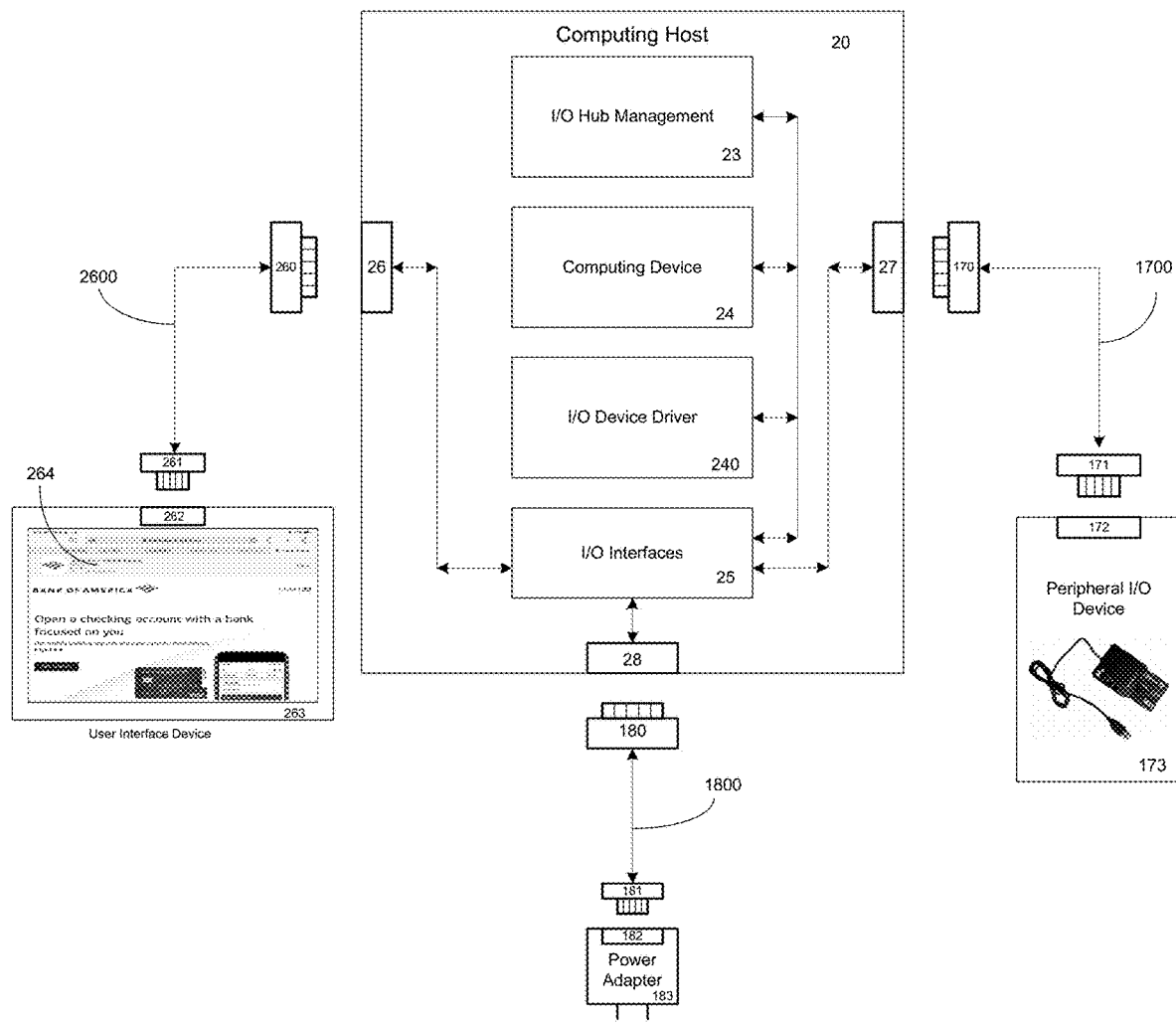
FIG. 1 illustrates a conventional example of a computing host with I/O device driver associated with the legacy I/O device.

As shown in FIG. 1, a conventional example of a computing host 20, includes a computing device 24, I/O hub management 23, I/O device driver 240, I/O interfaces 25, and interface connection 26, 27, 28. The computing host 20 may be powered through the interface connection 28 and the interface channel 1800, which includes interface connections 180, 181 and connects to a power adapter 183, through the interface connection 182. The computing host 20 further connects through the interface connection 27 and the interface channel 1700, which includes interface connections 170, 171 and connects to a legacy I/O device 173, through the interface connection 172. The computing host 20 also connects through the interface connection 26 and the interface channel 2600, which includes interface connections 260, 261 and connects to a user interface device 263, through the interface connection 262.

Also, as shown in FIG. 1, the corresponding I/O device driver 240 is required in order to associate with the legacy I/O device, which may be, for example, a smart card reader, 173. An application utility 264 is also required to install on the computing host 20, and run on the user interface device 263, in order for the user to perform the intended smart card reader functions.

The legacy peripheral I/O devices and the medical and industrial peripheral I/O devices generally work similarly as the smart card reader described above, in association with the computing host 20 and the user interface device 263. The difference between how the computing host 20 accesses two different peripheral I/O devices, resides in having different I/O device drivers 240 and the corresponding application utilities 264.

Figure 2:
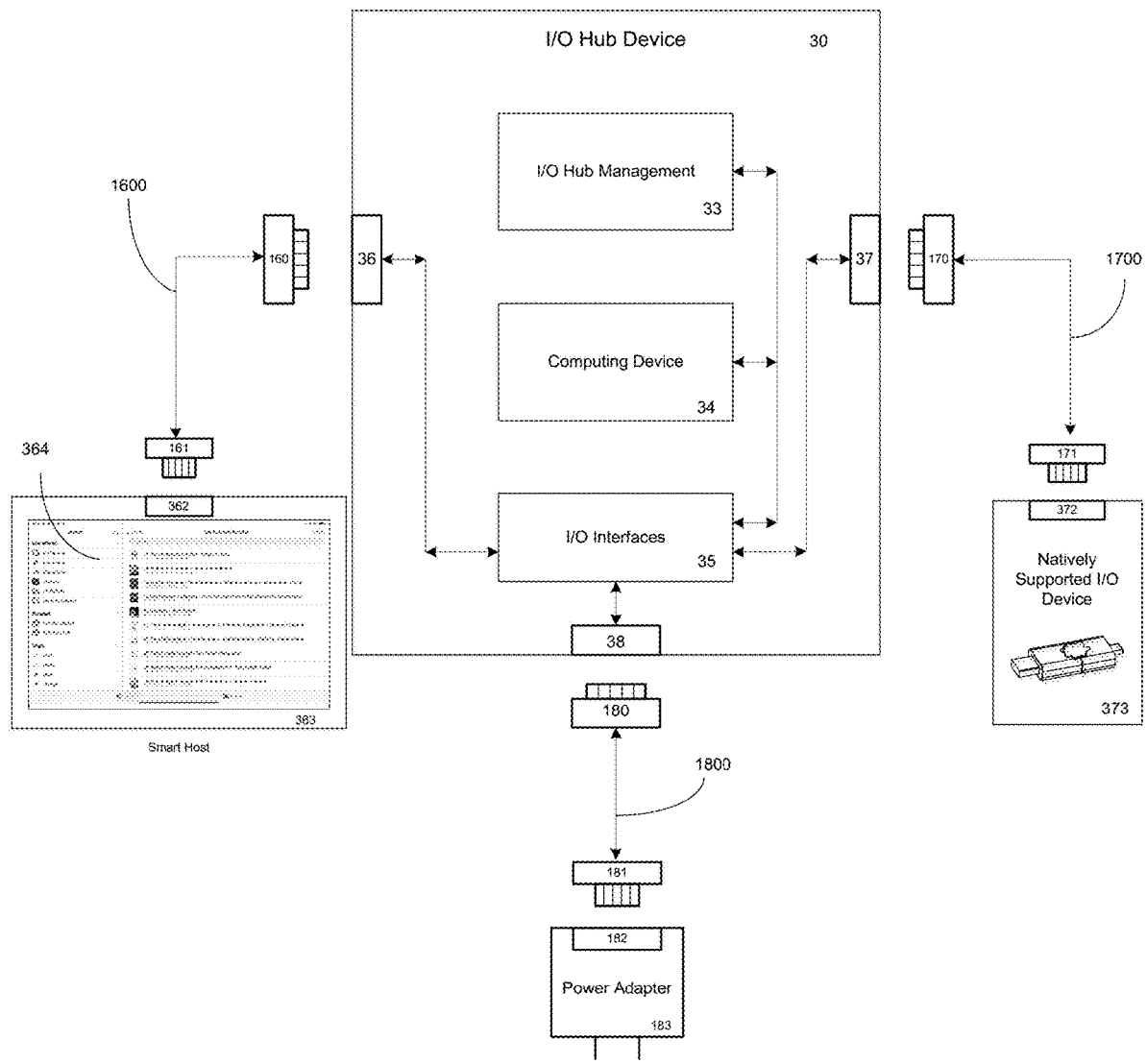
FIG. 2 illustrates a conventional example of a smart host, interfaced with an I/O hub device associated with the natively supported I/O device.

As shown in FIG. 2, a conventional example of an I/O hub device 30 includes computing device 34, I/O hub management 33, I/O interfaces 35, and interface connections 36, 37, 38. The I/O hub device 30 is powered through the interface connection 38 and the interface channel 1800, which includes interface connections 180, 181 and connects to a power adapter 183, through the interface connection 182. The I/O hub device further connects through the interface connection 37 and the interface channel 1700, which includes interface connections 170, 171 and connects to a natively supported I/O device 373, through the interface connection 372. The I/O hub device 30 also connects through the interface connection 36 and the interface channel 1600, which includes interface connections 160, 161 and connects to a smart host 363, through the interface connection 362.

As shown in FIG. 2, the smart host 363 is in place of the user interface device 263 and the I/O device driver 240 of FIG. 1. Due to the close nature of the smart host platform, it has very limited natively supported I/O devices 373 on its compatibility list. One example as shown is the standard USB storage 373. A native application utility 364, such as the File app on iOS, is also required on the smart host 363, in order for the user to perform the file explorer functions. Further, an application utility is also required to install on the smart host, in order for the user to interact with the natively supported I/O device 373.

Due to natively supported I/O devices being limited on the smart host 363, most of the legacy peripheral I/O devices and the medical and industrial peripheral I/O devices are not available on the smart host platforms. Those limited available ones are further curtailed due to the sandbox effect of the smart host platform security concern. In other words, even if the peripheral I/O device, such as the legacy USB storage 373 is recognized by the smart host 363, it cannot perform other useful functions such as backup and restore, beyond what was allowed by the natively supported File app, which only allows the stored content in the USB storage 373 to be explored and played on the smart host 363.

Figure 3:
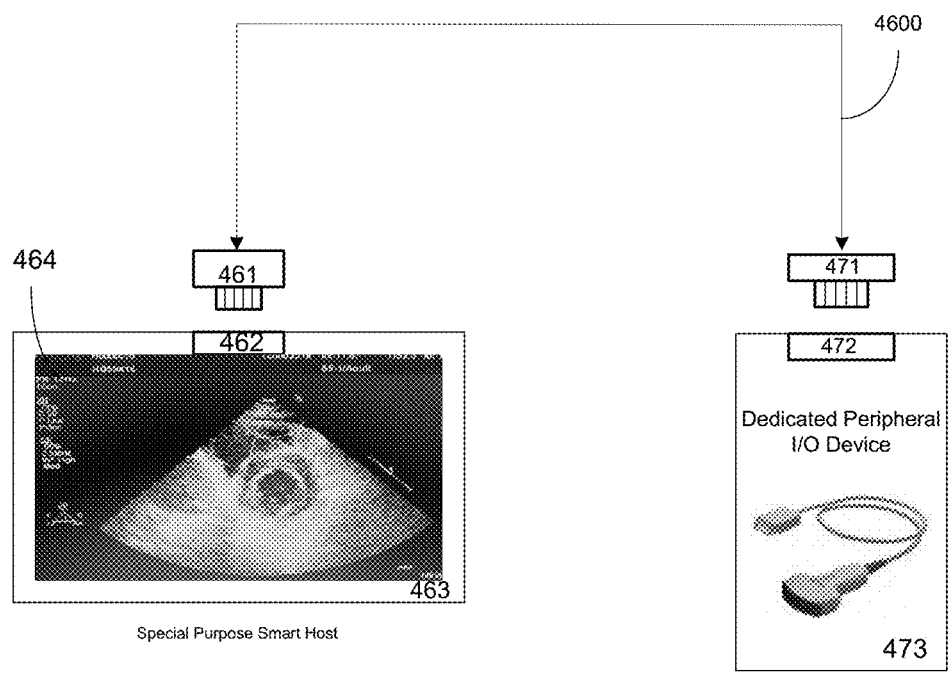
FIG. 3 illustrates a conventional example of a special purpose smart host used to connect to the dedicated peripheral I/O device.

As shown in FIG. 3, a conventional example of a special purpose smart host 463 is used to connect to the dedicated peripheral I/O device 473, through interface channel 4600. The interface channel 4600 has two interface connections 461, 471. One of the ends of the interface channel 4600 connects to the interface connection 462 of the special purpose smart host 463. Another end of the interface channel 4600 connects to the interface connection 472 of the dedicated peripheral I/O device 473. An application utility 464 is also required on the special purpose smart host 463, in order for the user to perform the targeted functions on the dedicated peripheral I/O device 473.

Due to the hardware compatibility issue with the dedicated peripheral I/O device 473, the special purpose smart host 464 has to be custom designed, in terms of computing power, user interface I/O, physical size, interface connections, device driver, firmware, OS and applications. Compared with the present embodiments and examples, the conventional art's downsides include rigid architecture, less flexibility in expansion, longer time in development and deployment, not scalable with advancement of technology, and relatively low in economy of scale that results in higher cost.

Figure 4:
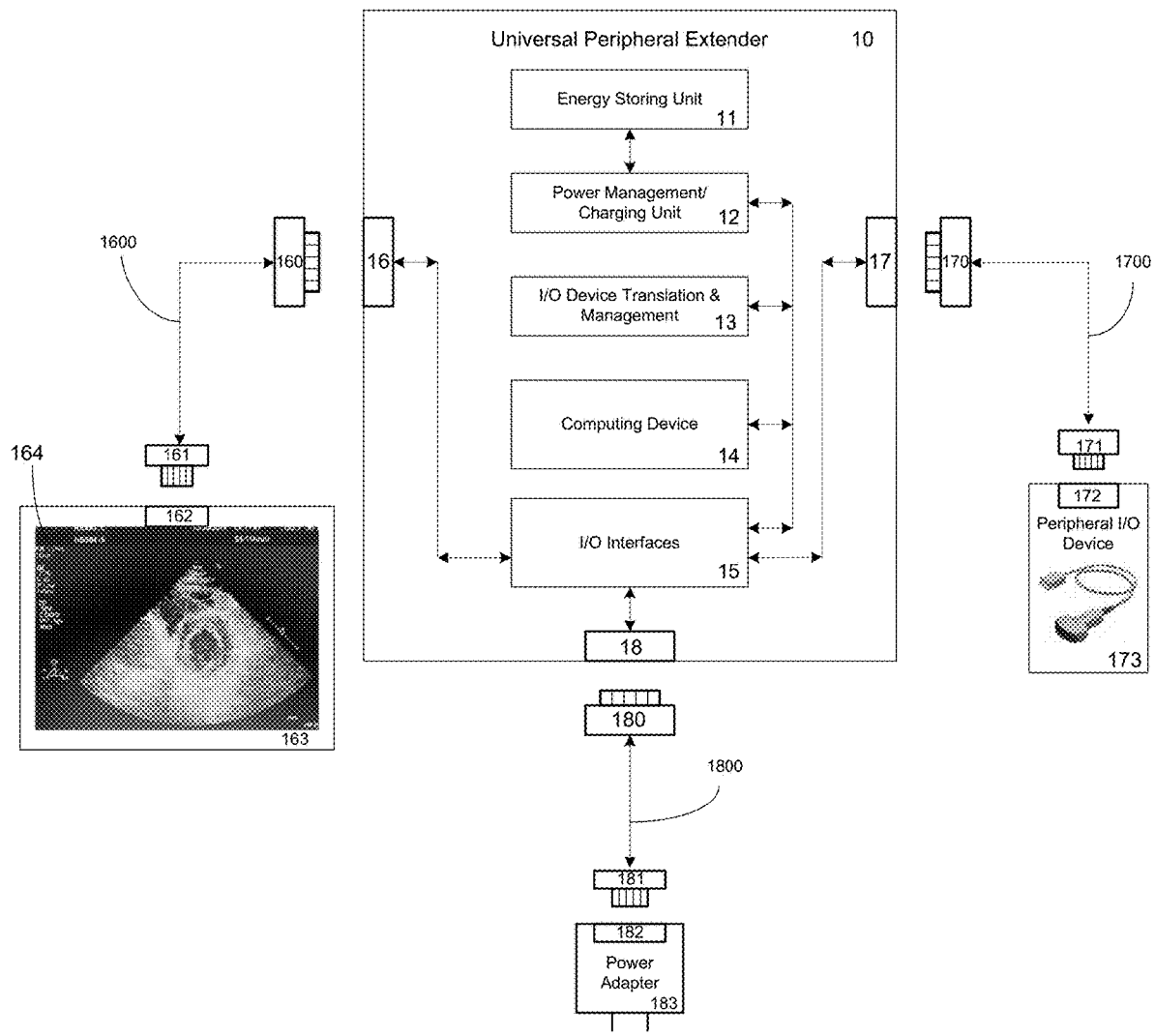
FIG. 4 illustrates an example of the universal peripheral extender architecture and system.

An example of the universal peripheral extender architecture and system as shown in FIG. 4, includes a universal peripheral extender 10, a plurality of smart hosts 163, a plurality of peripheral I/O devices 173, a plurality of interface channels 1600, 1700, 1800, a plurality of power sources 11, 12, 183, and at least one corresponding application utility 164.

The universal peripheral extender 10, further includes computing device 14, I/O device translation & management 13, I/O interfaces 15, energy storing unit 11, power management/charging unit 12, and interface connection 16, 17, 18. The universal peripheral extender 10 is powered through the interface connection 18 and the interface channel 1800, which includes interface connections 180, 181, and connects to a power adapter 183, through the interface connection 182. The universal peripheral extender 10 further connects through the interface connection 17 and the interface channel 1700, which includes interface connections 170, 171, and connects to a peripheral I/O device 173, through the interface connection 172. The universal peripheral extender 10 also connects through the interface connection 16 and the interface channel 1600, which includes interface connections 160, 161 and connects to a smart host 163, through the interface connection 162.

The smart host 163 may be a cell phone, a personal data assistant (PDA), a personal media player device, a wireless web-watch device, a personal headset device, an application specific device, or a hybrid device that includes any of the above functions. Smart host 163 may also be implemented as a personal computer including both laptop computer and non-laptop computer configurations.

The interface connection may be a physical or virtual connection that conforms to a specific interface in the hosts or the I/O devices. The interface channel, whether wired or wireless, may be interface connections between various hosts and I/O devices. The power source may be through an external power adapter 183, an internal power management/charging unit 12, or an energy storing unit 11.

As further shown in FIG. 4, the peripheral I/O device 173 may be a medical ultrasonic scanner probe endoscope, ultrasonic instrument, X-Ray, Electrocardiography (ECG) instrument, non-invasive blood glucose meter, Point-of-sale system, Contactless infrared thermometer, sphygmomanometer, AI co-processor, and others. An application utility 164, associated with the peripheral I/O device 173, is also utilized to install on the smart host 163, in order for the user to perform the medical ultrasonic instrument functions, such as ultrasonic image viewing.

The legacy peripheral I/O devices and the medical and industrial peripheral I/O devices generally work similarly as the ultrasonic scanner probe 173 as described above, in association with the universal peripheral extender 10 and the smart host 163. The difference between how the smart host 163 accesses two different peripheral I/O devices through the universal peripheral extender 10, resides in the peripheral I/O device 173 and the corresponding application utilities 164.

The examples and embodiments of the universal peripheral extender architecture and system brings many benefits compared with conventional art in the areas of flexibility in architecture, easier for expansion and upgrade, high performance, ubiquity, ease of development and deployment, smaller size, and standardization in high economy of scale resulting in lower cost.

Virtually all peripheral I/O devices are able to connect and deploy to the smart hosts without the original constraints imposed by the close nature of the smart host platforms by utilizing hardware mapping and translation on the universal peripheral extender, as well as the corresponding application utility running on the smart host for each intended peripheral I/O device.

Figure 5A:
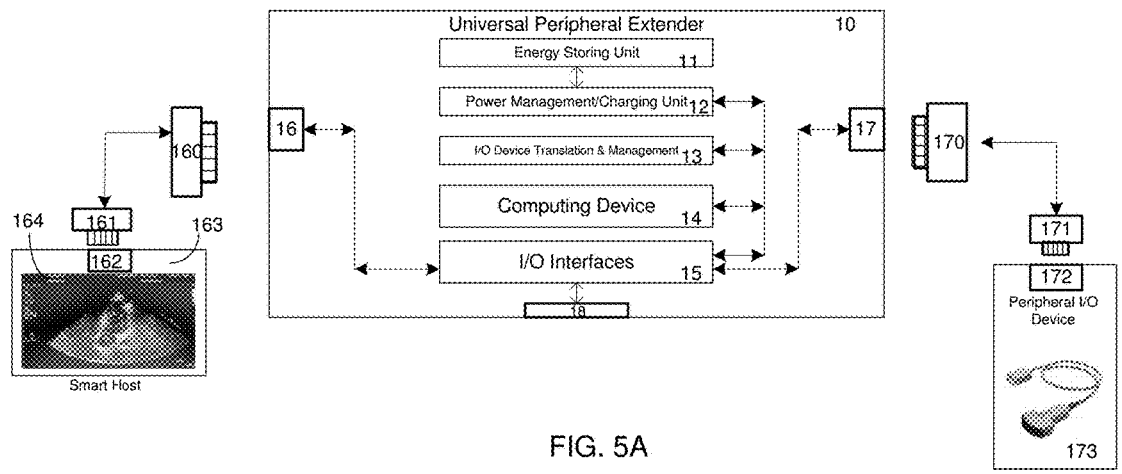
FIG. 5 illustrates examples of two physical connection combinations among the smart host, universal extender and the peripheral I/O device.
Figure 5B:
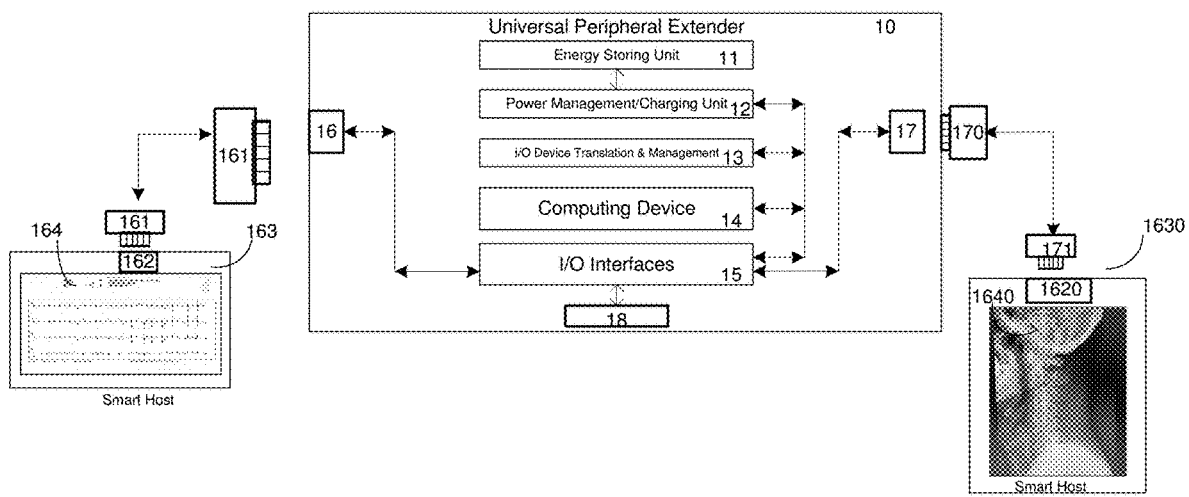

FIGS. 5A and 5B show examples of two physical connection combinations among a smart host, a universal extender and a peripheral I/O device. In both connection combinations, there requires at least one smart host for the user interface purpose.

FIG. 5A shows a smart host 163 connecting to a universal extender 10 and a peripheral I/O device 173. The universal peripheral extender 10 includes computing device 14, I/O device translation & management 13, I/O interfaces 15, energy storing unit 11, power management/charging unit 12, interface connection 16, 17, 18, and a corresponding application utility 164. The universal peripheral extender 10 is powered through the interface connection 18. The universal peripheral extender 10 further connects through the interface connection 17 and the interface channel 1700 (not shown), which includes interface connections 170, 171 and connects to a peripheral I/O device 173, through the interface connection 172. The universal peripheral extender 10 also connects through the interface connection 16 and the interface channel 1600 (not shown), which includes interface connections 160, 161 and connects to a smart host 163, through the interface connection 162. Interface connections 16, 17, 18 and 160, 161, 170, 171, may include, but are not limited to USB-A, PCIe, SATA, Ethernet, WiFi, Bluetooth, USB-C, Lightning, Thunderbolt, and HDMI. The peripheral I/O device 173 may be a medical ultrasonic scanner probe. An application utility 164, associated with the peripheral I/O device 173, is also utilized to install on the smart host 163, in order for the user to perform the medical ultrasonic instrument functions, such as ultrasonic image viewing.

FIG. 5B shows a smart host 163 connecting to a universal extender 10 and another smart host 1630. Other peripheral I/O devices may be connected but are not shown in FIG. 5B. If there is no other peripheral I/O device connected, then each smart host 163, 1630 can serve as a peripheral I/O device to the opposing smart host 1630, 163 through the I/O device translation & management 13 function in the universal peripheral extender 10. Interactive operations, including data transfer or backup restore functions between the two smart hosts 163, 1630 also may be utilized under this configuration. The universal peripheral extender 10, includes computing device 14, I/O device translation & management 13, I/O interfaces 15, energy storing unit 11, power management/charging unit 12, and interface connection 16, 17, 18 and a corresponding application utilities 164, 1640. The universal peripheral extender 10 is powered through the interface connection 18. The universal peripheral extender 10 connects through the interface connection 16 and the interface channel 1600 (not shown), which includes interface connections 160, 161 and connects to a smart host 163, through the interface connection 162. The universal peripheral extender 10 further connects through the interface connection 17 and the interface channel 1700 (not shown), which includes interface connections 170, 171 and connects to a smart host 1630, through the interface connection 1620. Interface connections 16, 17, 18 and 160, 161, 170, 171, may include, but are not limited to USB-A, PCIe, SATA, Ethernet, WiFi, Bluetooth, USB-C, Lightning, Thunderbolt, and HDMI. The application utility 164, is also utilized to install on the smart host 163, in order for the user to perform the medical ECG instrument functions, such as ECG image viewing. The application utility 1640, is also utilized to install on the smart host 1630, in order for the user to perform the X-Ray functions, such as X-Ray image viewing.

FIG. 6 shows the device control utility. Each peripheral I/O device includes the device control utility in order to communicate with the host through a specific interface. As shown in FIG. 6, the peripheral I/O device listens to the interface at 61. Next, the peripheral I/O device conducts a check to determine if the peripheral I/O device is discovered by the smart host at 62. If the peripheral I/O device is not discovered by the smart host (N), the peripheral I/O device returns to wait in the loop to listen to the interface at 61. If the peripheral I/O device is discovered by the smart host (Y), the peripheral I/O starts waiting for the smart host request at 63. The peripheral I/O device then processes the host request at 64. Afterwards, the peripheral I/O device conducts a check to determine if the host session ends at 65. If the host session is not ended, the peripheral I/O device returns to wait for the host request at 63. Otherwise, if the host session ends, the peripheral I/O device returns to listen to the interface at 61 and starts all over again.

FIG. 7 shows the smart host application utility process. Each peripheral I/O device includes the smart host-side utility in order to communicate with the smart host through a specific interface. As shown in FIG. 7, a smart host app executed by the smart host launches a target I/O Graphical User Interface (GUI) at 70. The smart host then enumerates the targeted peripheral (target) I/O device at 71. That is, enumerating the target I/O device is a process by which the target I/O device is attached to the universal peripheral extender system and is assigned a specific numerical address that will be used to access the target I/O device. It is also the time at which the smart host queries the target I/O device in order to decide what type of device the target I/O device is in order to attempt to assign an appropriate driver for the target I/O device. The smart host conducts a check to determine if the target I/O device is present at 72. If the target I/O device is not present, the process returns to enumerate the target I/O device again at 71. Otherwise, if the target I/O device is present, the smart host adds the target I/O device to the endpoint list at 73. The smart host then issues a RESET command to the target I/O device at 74. The smart host then obtains the Descriptor from the target I/O device at 75. For example, the Descriptor may be a USB Descriptor may include Device Descriptors, Configuration Descriptors, Interface Descriptors, Endpoint Descriptors, and String Descriptors. Afterwards, the smart hose assigns a device address to the target I/O device at 76. The smart host then obtains a whole Descriptor table from the target I/O device at 77. The smart host conducts a check to determine if the target I/O device is serviceable at 78. For example, USB devices have a hierarchy of descriptors which describe to the host information such as what the device is, who makes it, what version of USB it supports, how many ways it can be configured, the number of endpoints and their types etc. These descriptors define as the criteria inside the host, or inside the universal peripheral extender, if the device is serviceable. If the target I/O device is not serviceable, then an error is encountered at 780 and the process returns to enumerate the target I/O device again at 71. Otherwise, if the target I/O device is serviceable, the smart host activates the configurations on the target I/O device at 79. For example, the configurations (descriptor) specifies how the device is powered, what the maximum power consumption is, and the number of interfaces the device has. The smart host starts interacting with the target I/O device at 791. The smart host then conducts a check to determine if the application utility is to end at 793. If the application utility is to end, the utility exits. Otherwise, another check is conducted by the smart host to determine if the host session ends at 794. If the host session ends, the smart host process returns to enumerate the target I/O device again at 71. Otherwise, if the host session continues, the smart host continues interacting with the target I/O device at 791.

FIG. 8 shows the device-side I/O device translation & management utility. The universal peripheral extender includes the device-side I/O device translation & management utility in order to communicate with the target I/O device through a specific interface.

As shown in FIG. 8, the universal peripheral extender enumerates the target I/O device at 81. The universal peripheral extender conducts a check to determine if the target I/O device is present at 82. If the target I/O device is not present, the process returns to enumerate the target I/O device again at 81. Otherwise, if the device is present, the universal peripheral extender adds the target I/O device to the endpoint list at 83. The universal peripheral extender then issues a RESET command to the target I/O device at 84. The universal peripheral extender then obtains the Descriptor from the target I/O device at 85. Afterwards, the universal peripheral extender assigns a device address to the target I/O device at 86. The whole Descriptor table is then obtained from the target I/O device at 87. The universal peripheral extender conducts a check to determine if the target I/O device is serviceable at 88. If the target I/O device is not serviceable, then the universal peripheral extender encounters an error at 880 and the process returns to enumerate the target I/O device again at 81. Otherwise, if the target I/O device is serviceable, the universal peripheral extender activates the configurations on the target I/O device at 89. The universal peripheral extender then configures the target I/O device attributes in the translation & management tables at

890. The universal peripheral extender then starts interacting with the target I/O device at 891. The universal peripheral extender launches the host/device translation & management scheduler at 892. The universal peripheral extender then conducts a check to determine if the application utility is to end at 893. If the application utility is to end, the application utility exits. Otherwise, the universal peripheral extender conducts another check to determine if the host session ends at 894. If the host session ends, the process returns for the universal peripheral extender to enumerate the target I/O device again at 81. Otherwise, if the host session continues, the universal peripheral extender continues interacting with the target I/O device at 891.

FIG. 9 shows the host-side I/O device translation & management utility. The universal peripheral extender includes the host-side utility in order to communicate with the smart host through a specific interface.

As shown in FIG. 9, the universal peripheral extender listens to the interface at 91. Next, the universal peripheral extender conducts a check is to determine if the universal peripheral extender is discovered by the smart host at 92. If the universal peripheral extender is not discovered by the smart host, the process returns for the universal peripheral extender to wait in the loop to listen to the interface at 91. Otherwise, if the universal peripheral extender is discovered by the smart host, the universal peripheral extender starts configuring the host attributes in translation & management tables 920. For example, the universal peripheral extender behaves as the role of a device to the smart host. The universal peripheral extender will record the attributes from the host configuration including how the device is powered, what the maximum power consumption is, the number of interfaces it has, and the speed of the communication. The universal peripheral extender then waits for the smart host request at 93 and starts a host session at 930. The universal peripheral extender then processes the smart host request at 94. The universal peripheral extender launches the host/device translation & management scheduler at 940. For example, hardware mapping and translation as described in FIG. 8, FIG. 9, and FIG. 10 is associated with the enumeration of the target I/O device. Once the target I/O device is determined to be serviceable as in 88, the target I/O device attributes are recorded in the device map and table inside the universal peripheral extender as in 890. The target I/O device is then ready for translation to be serviceable to the request 94 from the smart host, as in 892 and 940. Afterwards, a check is conducted by the universal peripheral extender to determine if the host session ends at 95. If the host session does not end, the process for the universal peripheral extender returns to wait for the smart host request at 93. Otherwise, if the host session ends, the universal peripheral extender returns to listen to the interface at 91 and the process restarts.

FIG. 10 shows the host/device translation & management scheduler utility. The universal peripheral extender includes the host/device translation & management scheduler utility in order to schedule the smart host request and the target I/O device response through the specific interfaces.

As shown in FIG. 10, the universal peripheral extender looks up the host/device translation & management tables at 100. Next, a check is conducted by the universal peripheral extender to determine if the smart host and the target I/O device are compatible at 101. For example, if the host configuration attributes are not within the handling capabilities of the device, then the smart host and the target I/O device are not compatible. If the smart host and the target I/O device are not compatible, the universal peripheral extender ends the host session at 99. Otherwise, if the smart host and the target I/O device are compatible, the universal peripheral extender starts processing/scheduling host-side request from the smart host at 102. The universal peripheral extender then translates the smart host request for the target I/O device at 103 and passes the request to the target I/O device on the device-side at 104. For example, during translation, the universal peripheral extender behaves as a middleman between the smart host and the target I/O device. The smart host and the target I/O device do not recognize each other due to lack of native support from the host side. Once the universal peripheral extender validates the host request, the universal peripheral extender in turn assumes the role as a host to the target I/O device. The universal peripheral extender translates the original request from the host and pass it in the form or format that is understandable to the target I/O device. The universal peripheral extender then waits for the target I/O device response at 105 and translates the device response for the smart host at 106 and passes the response back to the smart host on the host-side at 107. After the response is passed back to the smart host, a check is conducted by the universal peripheral extender to determine if there is a command for the host session to end at 108. If the host session does not end, the universal peripheral extender returns to process and schedule the host-side request at 102. Otherwise, if the host session ends, the utility exits.

An additional examples include a smart host application system based on the universal peripheral extender architecture and system including a Portable ultrasonic image scanner, USB storage backup/restore system, Electrocardiography system, Smart card reader, Portable endoscope, Portable non-invasive blood glucose meter, Portable point-of-sale system, Portable sphygmomanometer, Contactless infrared thermometer, and AI Co-processor.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed examples or embodiments.

Furthermore, the present disclosure is not to be limited in terms of the particular examples or embodiments described in this application, which are intended as illustrations of various aspects. Many modifications and variations can be made without departing from its spirit and scope, as will be apparent to those skilled in the art. Functionally equivalent methods and even apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular examples or embodiments only, and is not intended to be limiting.

The computing operations, processes, etc. described herein may be implemented as computer-readable instructions stored on a computer-readable medium. The computer-readable instructions may, for example, be executed by a processor of a mobile unit, a network element, and/or any other computing device.

In an example, the computing device 14 typically includes one or more CPU processors and a system memory. A memory bus may be used for communicating between processor and system memory.

Data storage devices may be removable storage devices, non-removable storage devices, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory, removable storage devices, and non-removable storage devices are examples of computer storage media. Computer storage media may include, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 14. Any such computer storage media may be part of computing device 14.

Computing device 14 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 14 may also be implemented as a personal computer including both laptop computer and non-laptop computer configurations.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein may be implemented, e.g., hardware, software, and/or firmware, and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various examples or embodiments of the devices and/or processes for connecting the general-purpose peripheral I/O devices and the general-purpose smart host in legacy, medical, and industrial applications via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Those skilled in the art will recognize that some aspects of the examples or embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative example or embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a solid state drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

Lastly, with respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims, e.g., bodies of the appended claims, are generally intended as "open" terms, e.g., the term "including" should be interpreted as "including but not limited to," the term "having" should be interpreted as "having at least," the term "includes" should be interpreted as "includes but is not limited to," etc. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples or embodiments containing only one such recitation, even when the same claim includes the introductory phrases "one or more" or "at least one" and indefinite articles such as "a" or "an," e.g., "a" and/or "an" should be interpreted to mean "at least one" or "one or more;" the same holds true for the use of definite articles used to introduce claim recitations. In addition, even if a specific number of an introduced claim recitation is explicitly recited, those skilled in the art will recognize that such recitation should be interpreted to mean at least the recited number, e.g., the bare recitation of "two recitations," without other modifiers, means at least two recitations, or two or more recitations. Furthermore, in those instances where a convention analogous to "at least one of A, B, and C, etc." is used, in general such a construction is intended in the sense one having skill in the art would understand the convention, e.g., "a system having at least one of A, B, and C" would include but not be limited to systems that have A alone, B alone, C alone, A and B together, A and C together, B and C together, and/or A, B, and C together, etc. In those instances where a convention analogous to "at least one of A, B, or C, etc." is used, in general such a construction is intended in the sense one having skill in the art would understand the convention, e.g., "a system having at least one of A, B, or C" would include but not be limited to systems that have A alone, B alone, C alone, A and B together, A and C together, B and C together, and/or A, B, and C together, etc. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

From the foregoing, it will be appreciated that various examples or embodiments of the present disclosure have been described herein for purposes of illustration, and that various modifications may be made without departing from the scope and spirit of the present disclosure. Accordingly, the various examples or embodiments disclosed herein are not intended to be limiting, with the true scope and spirit being indicated by the following claims.

The invention claimed is:

1. A universal peripheral extender system, comprising:
    a universal peripheral extender, including:
        a computing device;
        an I/O device translation & management module;
        a plurality of I/O interfaces;
        an energy storing unit;
        a power management/charging unit; and
        a plurality of interface connections,
        wherein the I/O device translation & management module comprises:
            a device-side utility of the I/O device translation & management module;
            a host-side I/O device translation & management utility of the I/O device translation & management module; and
            a host/device translation & management scheduler utility;
    at least one interface channel;
    at least one smart host;
    at least one peripheral I/O device;
    at least one power source; and
    at least one corresponding application utility associated with at least one target I/O device, respectively;
    wherein the universal peripheral extender is communicatively coupled, via the at least one interface channel to: the at least one smart host, the target I/O device, and the at least one peripheral I/O device, respectively;
    wherein the at least one peripheral I/O device includes an interface connection communicatively coupled to the at least one interface channel;
    wherein the corresponding application utility associated with the target I/O device is installed in the at least one smart host to perform a function of the target I/O device,
    wherein the I/O device translation & management module including the device-side utility, that in response to execution, causes the computing device to perform operations comprising:
        enumerating the target I/O device;
        conducting a check to determine if the target I/O device is present;
        in response to the target I/O device not being present, returning the operations to the enumerating the target I/O device;
        in response to the target I/O device being present, adding the target I/O device to an endpoint list;
        issuing a RESET command to the target I/O device;
        obtaining a Descriptor from the target I/O device;
        assigning a device address to the target I/O device;
        obtaining a Descriptor table from the target I/O device;
        conducting a check to determine if the target I/O device is serviceable;
        in response to the target I/O device not being serviceable, then encountering an error and the process returns to the enumerating the target I/O device;
        in response to the target I/O device not being serviceable, then activating configurations on the target I/O device;
        configuring target I/O device attributes in target I/O device translation & management tables;
        interacting with the targeted I/O device;
        launching a host/device translation & management scheduler;
        conducting a check to determine if the application utility is to end;
        in response to the application utility ending, the application utility exits;
        in response to the application utility continuing, conducting another check to determine if the host session ends;
        in response to the host session ending, returning the operation to enumerating the target I/O device; and
        in response to the host session continuing, continue interacting with the target I/O device.

2. The universal peripheral extender system of claim 1, wherein the enumerating the target I/O device is a process by which the target I/O device is attached to the universal peripheral extender system and is assigned a specific numerical address that is used to access the target I/O device.

3. The universal peripheral extender system of claim 1, wherein the enumerating includes a time at which the smart host queries the target I/O device to decide what type of device the target I/O device is in order to assign an appropriate driver for the target I/O device.

4. A universal peripheral extender system, comprising:
a universal peripheral extender, including:
   a computing device;
   an I/O device translation & management module;
   a plurality of I/O interfaces;
   an energy storing unit;
   a power management/charging unit; and
   a plurality of interface connections,
   wherein the I/O device translation & management module comprises:
      a device-side utility of the I/O device translation & management module;
      a host-side I/O device translation & management utility of the I/O device translation & management module; and
      a host/device translation & management scheduler utility;
at least one interface channel;
at least one smart host;
at least one peripheral I/O device;
at least one power source; and
at least one corresponding application utility associated with a least one target device, respectively;
wherein the universal peripheral extender is communicatively coupled, via the at least one interface channel to: the at least one smart host, the target I/O device, and the at least one peripheral I/O device, respectively;
wherein the at least one peripheral I/O device includes an interface connection communicatively coupled to the at least one interface channel;
wherein the corresponding application utility associated with the target I/O device is installed in the at least one smart host to perform a function of the target device;
wherein the I/O device translation & management module including the a host-side I/O device translation & management utility, that in response to execution, causes the computing device to perform further operations comprising:
listening to the interface;
conducting a check is to determine if the universal peripheral extender is discovered by the at least one smart host;
in response to the universal peripheral extender not being discovered by the at least one smart host, returning the operation to waiting in a loop to the listening to the interface;
in response to the universal peripheral extender being discovered by the at least one smart host, configuring host/device attributes in host/device translation & management tables;
waiting for the smart host request;
in response to receiving the smart host request, starting a host session;
processing the smart host request;
launching a host/device translation & management scheduler;
conducting a check to determine if the host session ends;
in response to the host session not ending, returning the operation to the waiting for the smart host request;
in response to the host session ending, returning to the listening to the interface; and
restarting the operations.

5. A universal peripheral extender system, comprising:
a universal peripheral extender, including:
   a computing device;
   an I/O device translation & management module;
   a plurality of I/O interfaces;
   an energy storing unit;
   a power management/charging unit; and
   a plurality of interface connections,
   wherein the I/O device translation & management module comprises:
      a device-side utility of the I/O device translation & management module;
      a host-side I/O device translation & management utility of the I/O device translation & management module; and
      a host/device translation & management scheduler utility;
at least one interface channel;
at one smart host;
at least one peripheral I/O device;
at least one power source; and
at least one corresponding application utility associated with at least one target I/O device, respectively;
wherein the universal peripheral extender is communicatively coupled, via the at least one interface channel to: the at least one smart host, the target I/O device, and the at least one peripheral I/O device, respectively;
wherein the at least one peripheral I/O device includes an interface connection communicatively coupled to the at least one interface channel;
wherein the corresponding application utility associated with the target I/O device is installed in the at least one smart host to perform a function of the target I/O device;
wherein the I/O device translation & management module including the host/device translation & management scheduler utility, that in response to execution, causes the computing device to perform further operations comprising:
looking up the host/device translation & management tables;
conducting a check to determine if the at least one smart host and the target I/O device are compatible;
in response to the at least one smart host and the target I/O device not being compatible, ending the host session;
in response to the at least one smart host and the target I/O device being compatible, processing and scheduling host-side request from the at least one smart host;
translating the smart host request for the target I/O device;
passing the request to the target I/O device on the device-side;
waiting for the target I/O device response and translating the device response for the at least one smart host;
passing the response back to the at least one smart host on the host-side;
conducting a check to determine if there is a command to end the host session;
in response to the host session not ending, returning to processing and scheduling the host-side request;
in response to a command to end the host session, ending the host session and exiting.

6. A universal peripheral extender, comprising:
an I/O device translation & management module including:
   a device-side utility;
   a host-side I/O device translation & management utility; and a host/device translation & management scheduler utility; wherein executing the device-side utility of the I/O device translation & management module causes a computing device of the universal peripheral extender to perform operations comprising:
enumerating the target I/O device;
conducting a check to determine if the target I/O device is present;
in response to the target I/O device not being present, returning the operations to the enumerating the target I/O device;
in response to the target I/O device being present, adding the target I/O device to an endpoint list;
issuing a RESET command to the target I/O device;
obtaining a Descriptor from the target I/O device;
assigning a device address to the target I/O device;
obtaining a Descriptor table from the target I/O device;
conducting a check to determine if the target I/O device is serviceable;
in response to the target I/O device not being serviceable, then encountering an error and the process returns to the enumerating the target I/O device;
in response to the target I/O device not being serviceable, then activating configurations on the target I/O device;
configuring target I/O device attributes in target I/O device translation & management tables;
interacting with the targeted I/O device;
launching a host/device translation & management scheduler;
conducting a check to determine if the application utility is to end;
in response to the application utility ending, the application utility exits;
in response to the application utility continuing, conducting another check to determine if the host session ends;
in response to the host session ending, returning the operation to enumerating the target I/O device; and
in response to the host session continuing, continue interacting with the target I/O device.

7. A universal peripheral extender, comprising:
an I/O device translation & management module including:
a device-side utility;
a host-side I/O device translation & management utility; and
a host/device translation & management scheduler utility;
wherein executing the host-side I/O device translation & management utility of the I/O device translation & management module causes the computing device of the universal peripheral extender to perform operations comprising:
listening to an interface;
conducting a check is to determine if the universal peripheral extender is discovered by a smart host;
in response to the universal peripheral extender not being discovered by the smart host, returning the operation to waiting in a loop to the listening to the interface;
in response to the universal peripheral extender being discovered by the smart host, configuring host/device attributes in host/device translation & management tables;
waiting for a smart host request;
in response to receiving the smart host request, starting a host session;
processing the smart host request;
launching a host/device translation & management scheduler;
conducting a check to determine if the host session ends;
in response to the host session not ending, returning the operation to the waiting for the smart host request;
in response to the host session ending, returning to the listening to the interface; and
restarting the operations.

8. A universal peripheral extender, comprising:
an I/O device translation & management module including:
a device-side utility;
a host-side I/O device translation & management utility; and
a host/device translation & management scheduler utility;
wherein executing the host/device translation & management scheduler utility of the I/O device translation & management module causes the computing device of the universal peripheral extender to perform further operations comprising:
looking up host/device translation & management tables;
conducting a check to determine if a smart host and a target I/O device are compatible;
in response to the smart host and the target I/O device not being compatible, ending the host session;
in response to the smart host and the target I/O device being compatible, processing and scheduling host-side request from a smart host;
translating a smart host request for the target I/O device;
passing the smart host request to the target I/O device on the device-side;
waiting for the target I/O device response and translating the device response for the smart host;
passing the target I/O device response back to the smart host on the host-side;
conducting a check to determine if there is a command to end the host session;
in response to the host session not ending, returning to processing and scheduling the host-side request;
in response to a command to end the host session, ending the host session and exiting.

9. A non-transitory computer-readable medium storing executable instructions to communicatively connect a target I/O device and a smart host by an I/O device translation & management module of a universal peripheral extender so that, in response to execution, cause a computing device of the universal peripheral extender to execute a device-side utility of the I/O device translation & management module to perform operations comprising:
enumerating the target I/O device;
conducting a check to determine if the target I/O device is present;
in response to the target I/O device not being present, returning the operations to the enumerating the target I/O device;
in response to the target I/O device being present, adding the target I/O device to an endpoint list;
issuing a RESET command to the target I/O device;
obtaining a Descriptor from the target I/O device;
assigning a device address to the target I/O device;
obtaining a Descriptor table from the target I/O device;
conducting a check to determine if the target I/O device is serviceable;
in response to the target I/O device not being serviceable, then encountering an error and the process returns to the enumerating the target I/O device;
in response to the target I/O device not being serviceable, then activating configurations on the target I/O device;

configuring target I/O device attributes in target I/O device translation & management tables;
interacting with the targeted I/O device;
launching a host/device translation & management scheduler;
conducting a check to determine if the application utility is to end;
in response to the application utility ending, the application utility exits;
in response to the application utility continuing, conducting another check to determine if the host session ends;
in response to the host session ending, returning the operation to enumerating the target I/O device; and
in response to the host session continuing, continue interacting with the target I/O device.

10. The non-transitory computer-readable medium of claim 9, storing further executable instructions to communicatively connect the target I/O device and the smart host by the I/O device translation & management module of the universal peripheral extender so that, in response to execution, cause the computing device of the universal peripheral extender to execute a host-side I/O device translation & management utility of the I/O device translation & management module to perform further operations comprising:
listening to the interface;
conducting a check is to determine if the universal peripheral extender is discovered by the smart host;
in response to the universal peripheral extender not being discovered by the smart host, returning the operation to waiting in a loop to the listening to the interface;
in response to the universal peripheral extender being discovered by the smart host, configuring host/device attributes in host/device translation & management tables;
waiting for a smart host request;
in response to receiving the smart host request, starting a host session;
processing the smart host request;
launching a host/device translation & management scheduler;
conducting a check to determine if the host session ends;
in response to the host session not ending, returning the operation to the waiting for the smart host request;
in response to the host session ending, returning to the listening to the interface; and
restarting the operations.

11. The non-transitory computer-readable medium of claim 10, storing further executable instructions to communicatively connect the target I/O device and smart host by the I/O device translation & management module of the universal peripheral extender so that, in response to execution, cause the computing device of the universal peripheral extender to execute a host/device translation & management scheduler utility of the I/O device translation & management module to perform further operations comprising:
looking up the host/device translation & management tables;
conducting a check to determine if the smart host and the target I/O device are compatible;
in response to the smart host and the target I/O device not being compatible, ending the host session;
in response to the smart host and the target I/O device being compatible, processing and scheduling a host-side request from the smart host;
translating the smart host request for the target I/O device;
passing the request to the target I/O device on the device-side;
waiting for the target I/O device response and translating the device response for the smart host;
passing the response back to the smart host on the host-side;
conducting a check to determine if there is a command to end the host session;
in response to the host session not ending, returning to processing and scheduling the host-side request;
in response to a command to end the host session, ending the host session and exiting.

\* \* \* \* \*